(12) United States Patent
Pinsky et al.

(10) Patent No.: US 11,441,955 B2
(45) Date of Patent: Sep. 13, 2022

(54) WASH AND LIVESTOCK MONITORING MILK METER

(71) Applicant: Afimilk Agricultural Cooperative Ltd., Kibutz Afikim (IL)

(72) Inventors: Niv Pinsky, Kibutz Afikim (IL); Ehud Golan, Gilon (IL); Itamar Cohen, Givat Yoav (IL)

(73) Assignee: AFIMILK AGRICULTURAL COOPERATIVE LTD., Kibbutz Afikim (IL)

( * ) Notice: Subject to any disclaimer, the term of this patent is extended or adjusted under 35 U.S.C. 154(b) by 353 days.

(21) Appl. No.: 16/796,242

(22) Filed: Feb. 20, 2020

(65) Prior Publication Data
US 2021/0262869 A1    Aug. 26, 2021

(51) Int. Cl.
G01K 13/02     (2021.01)
G01K 3/00      (2006.01)
G01N 27/10     (2006.01)
G01N 33/04     (2006.01)
G01N 33/14     (2006.01)
A01J 9/00      (2006.01)

(52) U.S. Cl.
CPC .............. *G01K 13/02* (2013.01); *A01J 9/00* (2013.01); *G01K 3/005* (2013.01); *G01N 27/10* (2013.01); *G01N 33/04* (2013.01); *G01N 33/14* (2013.01); *G01K 13/026* (2021.01)

(58) Field of Classification Search
CPC ...... G01K 13/02; G01K 3/005; G01K 13/026; A01J 9/00; A01J 5/01; G01N 27/10; G01N 33/04; G01N 33/14
See application file for complete search history.

(56) References Cited

U.S. PATENT DOCUMENTS

| | | | |
|---|---|---|---|
| 2003/0146834 A1* | 8/2003 | Stevens | A01J 5/007 340/521 |
| 2015/0241336 A1* | 8/2015 | Krief | G01N 21/25 356/409 |
| 2016/0108388 A1* | 4/2016 | Babe | D06L 4/40 435/252.35 |
| 2017/0172101 A1* | 6/2017 | Kool | A01K 5/02 |
| 2019/0021548 A1* | 1/2019 | Eisner | A61J 11/04 |
| 2021/0176950 A1* | 6/2021 | Jensen | A01J 9/04 |

* cited by examiner

*Primary Examiner* — Christopher P McAndrew
*Assistant Examiner* — Zannatul Ferdous
(74) *Attorney, Agent, or Firm* — The Roy Gross Law Firm, LLC; Roy Gross

(57) ABSTRACT

Disclosed is a monitoring milk meter, which is able to monitor the livestock being milked, as well as general procedures performed in the milking farm, such as the CIP procedure.

8 Claims, 10 Drawing Sheets

WASH AND LIVESTOCK MONITORING MILK METER

FIELD OF THE INVENTION

The present invention is directed to a wash and livestock monitoring milk meter. In particular, the present invention is directed to a milk meter that includes a temperature sensor and optionally a conductivity sensor for monitoring (a) the cleaning in place (CIP) washing process of the dairy milking system; (b) the livestock being milked; or both.

BACKGROUND OF THE INVENTION

Food safety and public health regulations around the world require that any surfaces that come in contact with food and/or drinks must be regularly cleaned in order to avoid food contamination and bacteria growth. The procedure for the internal sanitation of production facilities is known as "clean in place" or CIP, wherein the CIP procedure may be either automatic or semi-automatic, and is implemented during production, without dismantling equipment, or the like.

The most common CIP procedures require that all internal surfaces, which come in contact with the food/drinks are covered, during the CIP process, with active sanitization chemicals. CIP processes in dairy milking systems commonly ensure all of the following:

Coverage—applying full coverage of the active solution(s) to all surfaces in contact with milk.
Time—allowing the required time for the solution to act on the surface.
Temperature—ensuring the ideal temperature for the optimal performance of the active component in the wash solution, as per the manufacturer's recommendation.
Concentration—providing the correct concentration of the active agent in the wash solution.

Common CIP procedures are generally performed two to three times a day, between milking sessions, and usually include the following cycles:

1. Initial Rinse Cycle—removes milk residue from the system. This cycle circulates lukewarm water prior to running hot water through the system, thus avoiding the "baking" of milk protein onto surfaces.
2. Acid Cycle—circulates hot water mixed with acid (usually caustic soda) for removing soil and preventing the buildup of milk-stone inside the system.
3. Sanitizing Cycle—circulates hot water mixed with disinfectant(s) for killing bacteria.
4. Final Rinse—runs cold water through the system for removing any trace of disinfectant solution prior the next milking session.

However, generally, the CIP is not monitored in milk farms and therefore, the milk farms will only become aware of malfunction in the CIP wash procedure in view of contaminations found in the milk, which could lead to high loses for the milk farm. This could be especially hazardous in large milking farms. For instance, even if there were a central wash monitoring system in the milk farm, that system could not necessarily detect malfunctions of the wash procedure, since there is a large distance between the first and last stall, and a central monitoring system would only be able to detect one point. Particularly under cold conditions, even in smaller milking farms, the common CIP procedures may not be appropriate. For instance, under cold conditions the temperature of the wash fluid may drop between the entry point and the exit point; however, without a proper monitoring system the milk farm system may not detect such a temperature fluctuation. Such temperature fluctuations may require additional measures to be performed in order for the milking system to be properly washed, e.g., performing additional washings, using wash liquids with higher starting temperatures and/or utilizing longer lengths of washing times. Without the detection of such temperature fluctuations the milking system may not be properly washed, leading to possible milk contamination.

Further, while complex monitoring systems may be in place in milk farms in order to monitor the livestock, those systems generally require a tag to be attached to each animal, without which the animal cannot be monitored. Thus, if an animal loses its tag, or if the tag malfunctions, the milking farm system will be "blind" to that animal.

Accordingly, there is a need in the art for a milking system that provides monitoring means, which will provide monitoring to multiple points within the milking farm, such that general procedures, such as the CIP procedures, may be properly monitored and further, such that the livestock may be monitored, without dependency on tags and the like.

SUMMARY OF THE INVENTION

Embodiments of the invention are directed to a milk meter comprising a temperature sensor.

According to some embodiments, the milk meter further comprises a conductivity sensor. According to further embodiments, the milk meter further comprises a turbidity sensor.

Further embodiments of the invention are directed to a system comprising:

a first plurality of milk meters, wherein each milk meter in the first plurality of milk meters comprises a temperature sensor; and a central computer system connected to the plurality of milk meters;

wherein the central computer system is connected physical or virtually to the milk meters and wherein the central computer system is configured to:

store at least one predefined temperature value, at least one predefined temperature time length value, at least one predefined temperature range, at least one predefined temperature threshold and at least one predefined temperature time length threshold;
receive and store temperature measurements from the temperature sensors;
compare the temperature measurements to the predefined temperature value;
calculate temperature time length measurements according to a time during which the temperature measurements are within about the predetermined temperature range;
generate a temperature alert when a deviation between the temperature measurements and the predefined temperature value is above about the predefined temperature threshold;
generate a temperature time alert when a deviation between the temperature time length measurements and the predefined temperature time length value is above about the predefined temperature time length threshold.

According to some embodiments, the system further comprises a second plurality of milk meters, wherein
each milk meter in the second plurality of milk meters comprises a conductivity sensor; and
wherein the central computer system is further configured to:

store at least one predefined conductivity value, at least one predefined conductivity time length value, at least one predefined conductivity range, at least one predefined conductivity threshold and at least one predefined conductivity time length threshold;

receive and store conductivity measurements from the conductivity sensors;

compare the conductivity measurements to the predefined conductivity value;

calculate conductivity time length measurements according to a time during which the conductivity measurements are within about the predetermined conductivity range;

generate conductivity alerts when a deviation between the conductivity measurements and the predefined conductivity value is above about the predefined conductivity threshold;

generate conductivity time alerts when a deviation between the conductivity time length measurements and the predefined conductivity time length values is above about the predefined conductivity time length threshold.

According to some embodiments, the first plurality of milk meters and the second plurality of milk meters are the same, such that each milk meter includes both a temperature sensor and a conductivity sensor.

According to some embodiments, the system further comprises a third plurality of milk meters, wherein each milk meter in the third plurality of milk meters comprises a turbidity sensor; and wherein the central computer system is further configured to:

store at least one predefined turbidity value, at least one predefined turbidity time length value, at least one predefined turbidity range, at least one predefined turbidity threshold and at least one predefined turbidity time length threshold;

receive and store turbidity measurements from the conductivity sensors;

compare the turbidity measurements to the predefined conductivity value;

calculate turbidity time length measurements according to a time during which the turbidity measurements are within about the predetermined turbidity range;

generate turbidity alerts when a deviation between the turbidity measurements and the predefined turbidity value is above about the predefined turbidity threshold;

generate turbidity time alerts when a deviation between the turbidity time length measurements and the predefined turbidity time length values is above about the predefined turbidity time length threshold.

According to some embodiments, the first plurality of milk meters, the second plurality of milk meters and the third plurality of milk meters are the same, such that each milk meter includes a temperature sensor, a conductivity sensor and a turbidity sensor.

Further embodiments of the invention are directed to a method for monitoring a CIP wash procedure in a milk farm, wherein the method comprises:

measuring the temperature of a wash fluid by way of a temperature sensor positioned within each milk meter in a plurality of milk meters, thereby providing temperature measurements; and sending the temperature measurements from each milk meter in the plurality of milk meters to a central computer system at pre-defined time intervals.

According to some embodiments, the method further comprises:

comparing the obtained temperature measurements to at least one predefined temperature value; and generating a temperature alert when a deviation between the obtained temperature measurements and the predefined temperature value is above about a pre-defined temperature threshold.

According to some embodiments, the method further comprises:

calculating the length of time during which the temperature measurements are within about a predetermined temperature range, thereby obtaining a temperature time length measurement.

According to some embodiments, the method further comprises:

comparing the obtained temperature measurements to at least one predefined temperature value;

comparing the obtained temperature time length measurements to at least one predefined temperature time length value;

generating a temperature alert when a deviation between the temperature measurement and the pre-defined temperature value is above about a predefined temperature threshold;

generating a temperature time alert when a deviation between the temperature time length measurement and the predefined temperature time length value is above about a pre-defined temperature time threshold; or any combination thereof.

Additional embodiments of the invention are directed to a method for monitoring a CIP wash procedure in a milk farm, wherein the method comprises:

measuring the temperature of a wash fluid by way of a temperature sensor positioned within each milk meter in a first plurality of milk meters, thereby obtaining temperature measurements;

measuring the conductivity of the wash fluid by way of a conductivity sensor positioned within each milk meter in a second plurality of milk meters, thereby obtaining conductivity measurements; and sending the temperature measurements and conductivity measurements from each temperature sensor and each conductivity sensor to a central computer system, at pre-defined time intervals, wherein the time intervals for sending the temperature measurements may be the same or different than the time intervals for sending the conductivity measurements, wherein the first plurality of milk meters and the second plurality of milk meters may be the same or different.

According to some embodiments, the method further comprises:

comparing the obtained temperature measurements to at least one predefined temperature value;

comparing the obtained conductivity measurements to at least one predefined conductivity value;

generating a temperature alert when a deviation between the obtained temperature measurements and the predefined temperature value is above about a pre-defined temperature threshold;

generating a conductivity alert when a deviation between the obtained conductivity measurements and the predefined conductivity value is above about a pre-defined conductivity threshold; or any combination thereof.

According to some embodiments, the pH of the wash fluid is calculated from the conductivity measurements.

Further embodiments of the invention are directed to a method for monitoring a CIP wash procedure in a milk farm, wherein the method comprises:

measuring the temperature of a wash fluid by way of a temperature sensor positioned within each milk meter in a first plurality of milk meters, thereby obtaining temperature measurements;

measuring the conductivity of the wash fluid by way of a conductivity sensor positioned within each milk meter in a second plurality of milk meters, thereby obtaining conductivity measurements;

sending the temperature measurements and conductivity measurements from each temperature sensor and each conductivity sensor to a central computer system at pre-defined time intervals, wherein the time intervals for sending the temperature measurements may be the same or different than the time intervals for sending the conductivity measurements;

calculating the length of time during which the temperature measurements are within about a predetermined temperature range, thereby obtaining a temperature time length measurement; and calculating the length of time during which the conductivity measurements are within about a predetermined conductivity range, thereby obtaining a conductivity time length measurement, wherein the first plurality of milk meters and the second plurality of milk meters may be the same or different.

According to some embodiments, the method further comprises:

generating a temperature alert when a deviation between the temperature measurement and the pre-defined temperature value is above about a predefined temperature threshold;

generating a conductivity alert when a deviation between the conductivity measurement and the pre-defined conductivity value is above about a predefined conductivity threshold;

generating a temperature time alert when a deviation between the temperature time length measurement and the predefined temperature time length values is above about a pre-defined temperature time threshold;

generating a conductivity time alert when a deviation between the conductivity time length measurement and the predefined conductivity time length values is above about a pre-defined conductivity time threshold; or any combination thereof.

According to some embodiments, the method further comprises altering the CIP wash procedure according to the temperature alerts, the temperature time alerts, the conductivity alerts, the conductivity time alerts, or any combination thereof.

According to some embodiments, the method further comprising:

measuring the turbidity of the wash fluid by way of a turbidity sensor positioned within each milk meter in a third plurality of milk meters, thereby obtaining turbidity measurements;

sending the turbidity measurements from each turbidity sensor to a central computer system at pre-defined time intervals, wherein the time intervals for sending the temperature measurements, conductivity measurements and turbidity measurements may be the same or different; and calculating the length of time during which the turbidity measurements are within about a predetermined turbidity range, thereby obtaining a turbidity time length measurement, wherein the first plurality of milk meters, the second plurality of milk meters and the third plurality of milk meters may be the same or different.

According to some embodiments, the method further comprises:

generating a turbidity alert when a deviation between the turbidity measurement and the pre-defined turbidity value is above about a predefined turbidity threshold;

generating a turbidity time alert when a deviation between the turbidity time length measurement and the pre-defined turbidity time length values is above about a pre-defined turbidity time threshold; or any combination thereof.

According to some embodiments, the method further comprises altering the CIP wash procedure according to the temperature alerts, the temperature time alerts, the conductivity alerts, the conductivity time alerts, the turbidity alerts, the turbidity time alerts, or any combination thereof.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

Figure 1:
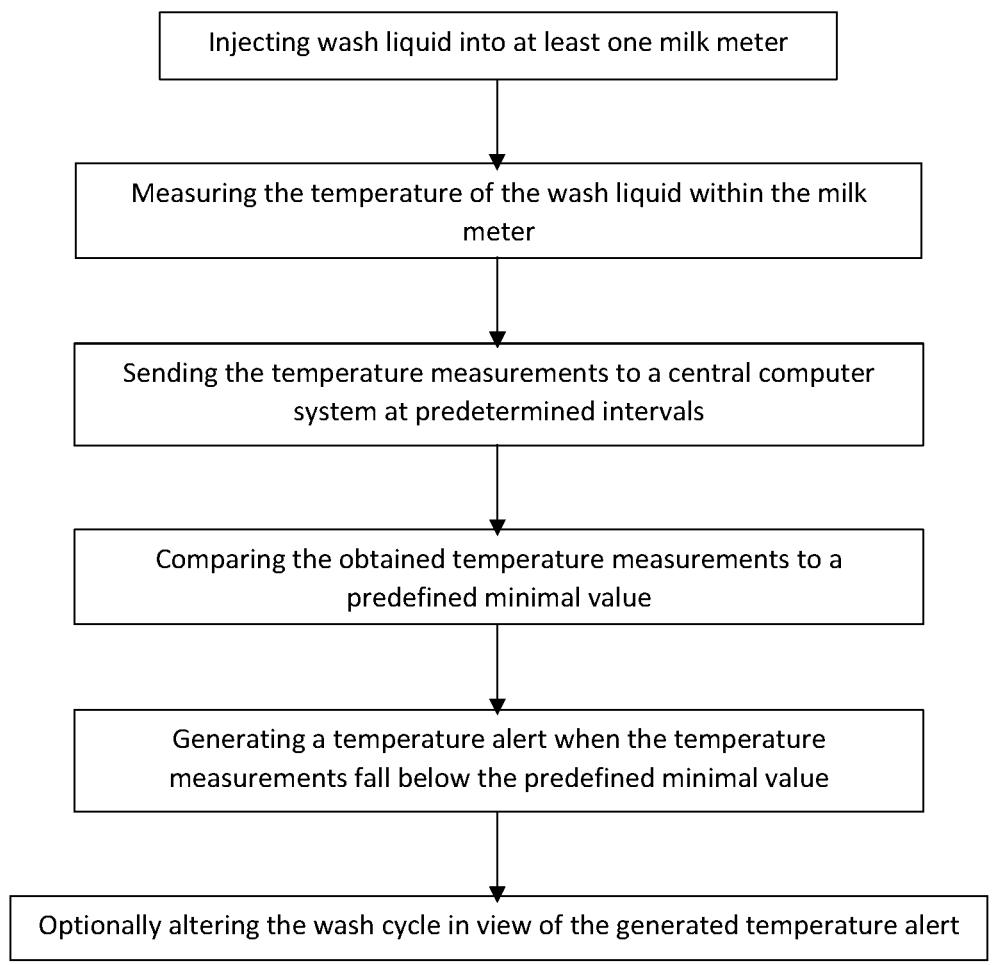
FIG. 1 presents a flow chart detailing an embodiment of the method of the invention, utilizing temperature measurements.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

It is noted that throughout this document, the term "about" is intended to cover ±10% of the disclosed value. It is further noted that throughout this document, the terms computer system and central computer system are interchangeable and refer to any computerized system that may receive data, store data, perform calculations, and the like. For instance, the computer system, or the centralized computer system, may be a smartphone, a laptop, a tablet, a PC, a dedicated computerized system in the milk farm, a remote dedicated computerized system or the like. Further, even where one computer system is mentioned, this is meant to additionally refer to several computerized systems connected to one another, such that, e.g., alerts may be sent to one system, e.g., a user's smartphone, while calculation are performed on a second system, e.g., a dedicated computerized system in the milk farm or remote thereto.

The term "predefined" in any context, such as "predefined temperature value", "predefined conductivity value", "predefined turbidity value", "predefined temperature threshold", "predefined conductivity threshold", "predefined turbidity threshold", and the like, are values, thresholds and the like that may be set, reset and changed at any time by an authorized user.

Embodiments of the invention are directed to a milk meter that includes a temperature sensor. According to some embodiments, the milk meter further comprises a conductivity sensor. According to additional embodiments, the milk meter further comprises a turbidity sensor.

Further embodiments of the invention are directed to a method for monitoring the body temperature of livestock in a milk farm, while being milked, wherein the method comprises measuring the temperature of the milk in the milk meter and deducing the body temperature of the livestock being milked therefrom.

Additional embodiments of the invention are directed to a method for monitoring the conductivity of the milk within each milk meter in a plurality of milk meters and deducing the pH of the milk therefrom. Further embodiments of the invention are directed to a method for monitoring the turbidity of the milk within each milk meter in a plurality of milk meters. It is noted that the turbidity of the milk may change due to contaminations in the milk, and may possibly indicate illness of the animal being milked.

According to some embodiments, the method of the invention includes monitoring the temperature, the conductivity and/or the turbidity of the milk in each milk meter in a plurality of milk meters, and deducing the body temperature of the animal being milked, the pH of the milk flowing through the milk meter, detecting contaminations, and any combination thereof.

Further embodiments of the invention are directed to a method for monitoring a CIP wash procedure in a milk farm, wherein the method comprises:
measuring the temperature of a wash fluid by way of a temperature sensor positioned within each milk meter in a plurality of milk meters, thereby providing temperature measurements; and
sending the temperature measurements from each milk meter in the plurality of milk meters to a central computer system at pre-defined time intervals.

According to some embodiments, the method for monitoring a CIP wash procedure further comprises:
comparing the obtained temperature measurements to at least one predefined temperature value stored in the central computer system; and
generating a temperature alert when a deviation between the obtained temperature measurements and the pre-defined temperature value is above about a pre-defined temperature threshold.

FIG. 1 presents a flowchart in which the above embodiment of the method of the invention is illustrated.

Further embodiments of the invention are directed to a method for monitoring a CIP wash procedure in a milk farm, wherein the method comprises:
measuring the turbidity of a wash fluid by way of a turbidity sensor positioned within each milk meter in a plurality of milk meters, thereby providing turbidity measurements; and
sending the turbidity measurements from each milk meter in the plurality of milk meters to a central computer system at pre-defined time intervals.

According to some embodiments, the method for monitoring a CIP wash procedure further comprises:
comparing the obtained turbidity measurements to at least one predefined turbidity value stored in the central computer system; and
generating a turbidity alert when a deviation between the obtained turbidity measurements and the predefined turbidity value is above about a pre-defined turbidity threshold.

Figure 2:
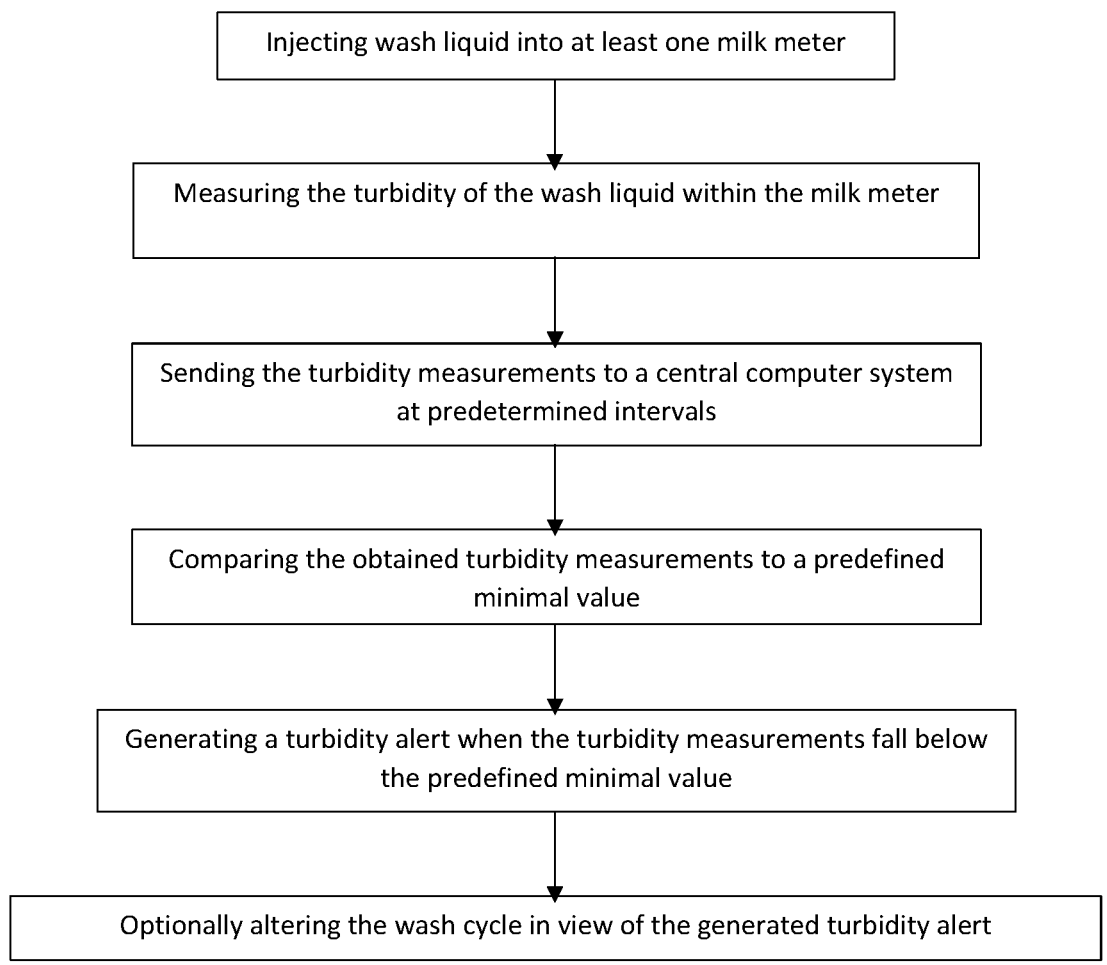
FIG. 2 presents a flow chart detailing an embodiment of the method of the invention, utilizing turbidity measurements.

FIG. 2 presents a flowchart in which the above embodiment of the method of the invention is illustrated.

Additional embodiments of the invention are directed to a method for monitoring a CIP wash procedure in a milk farm, wherein the method comprises:
measuring the temperature of a wash fluid by way of a temperature sensor positioned within each milk meter in a plurality of milk meters, thereby providing temperature measurements;
sending the temperature measurements from each milk meter in the plurality of milk meters to a central computer system at pre-defined time intervals;
calculating the length of time during which the temperature measurements are within about a predetermined temperature range, thereby obtaining a temperature time length measurement.

According to some embodiments, the method for monitoring a CIP wash procedure in a milk farm further comprises:
comparing the obtained temperature measurements to at least one predefined temperature value stored in the computer system;
comparing the obtained temperature time length measurements to at least one predefined temperature time length value stored in the computer system;
generating a temperature alert when a deviation between the temperature measurement and the pre-defined temperature value is above about a predefined temperature threshold;

generating a temperature time alert when a deviation between the temperature time length measurement and the predefined temperature time length value is above about a pre-defined temperature time threshold; or any combination thereof.

Additional embodiments of the invention are directed to a method for monitoring a CIP wash procedure in a milk farm, wherein the method comprises:

measuring the temperature of a wash fluid by way of a temperature sensor positioned within each milk meter in a plurality of milk meters, thereby obtaining temperature measurements;

measuring the conductivity of the wash fluid by way of a conductivity sensor positioned within each milk meter in the plurality of milk meters, thereby obtaining conductivity measurements; and sending the temperature measurements and conductivity measurements from each temperature sensor and conductivity sensor to a central computer system, at pre-defined time intervals, wherein the time intervals for sending the temperature measurements may be the same or different than the time intervals for sending the conductivity measurements.

It is noted that the plurality of milk meters may or may not include all milk meters in the milk farm. It is further noted that the temperature sensors may be placed in a first plurality of milk meters, while the conductivity sensors may be placed in a second plurality of milk meters, wherein the first and second plurality of milk meters may be the same, i.e., include the same milk meters, may overlap with one another, i.e., at least partially include the same milk meters, may not be the same, i.e., include only different milk meters. Accordingly, any milk meter in the milk farm may include a temperature sensor, a conductivity sensor, both a temperature sensor and a conductivity sensor or neither a temperature sensor nor a conductivity sensor. According to some embodiments all milk meters in the milk farm include both a temperature sensor and a conductivity sensor. Since there are multiple sensors throughout the milk farm, coverage measurements may be performed in order to determine the coverage of the wash throughout the milk farm.

Additional embodiments of the invention are directed to a method for monitoring a CIP wash procedure in a milk farm, wherein the method comprises:

measuring the temperature of a wash fluid by way of a temperature sensor positioned within each milk meter in a plurality of milk meters, thereby obtaining temperature measurements;

measuring the conductivity of the wash fluid by way of a conductivity sensor positioned within each milk meter in the plurality of milk meters, thereby obtaining conductivity measurements;

measuring the turbidity of the wash fluid by way of a turbidity sensor positioned within each milk meter in the plurality of milk meters, thereby obtaining conductivity measurements; and sending the temperature measurements, conductivity measurements and turbidity measurements from each temperature sensor, conductivity sensor and turbidity sensor to a central computer system, at pre-defined time intervals, wherein the time intervals for sending each one of the temperature measurements, the conductivity measurements and the turbidity measurements may be the same or different.

Additional embodiments of the invention are directed to a method for monitoring a CIP wash procedure in a milk farm, wherein the method comprises:

measuring the conductivity of the wash fluid by way of a conductivity sensor positioned within each milk meter in the plurality of milk meters, thereby obtaining conductivity measurements;

measuring the turbidity of the wash fluid by way of a turbidity sensor positioned within each milk meter in the plurality of milk meters, thereby obtaining conductivity measurements; and sending the conductivity measurements and turbidity measurements from each conductivity sensor and turbidity sensor to a central computer system, at pre-defined time intervals, wherein the time intervals for sending each one of the conductivity measurements and the turbidity measurements may be the same or different.

Additional embodiments of the invention are directed to a method for monitoring a CIP wash procedure in a milk farm, wherein the method comprises:

measuring the temperature of a wash fluid by way of a temperature sensor positioned within each milk meter in a plurality of milk meters, thereby obtaining temperature measurements;

measuring the turbidity of the wash fluid by way of a turbidity sensor positioned within each milk meter in the plurality of milk meters, thereby obtaining conductivity measurements; and sending the temperature measurements and turbidity measurements from each temperature sensor and turbidity sensor to a central computer system, at pre-defined time intervals, wherein the time intervals for sending each one of the temperature measurements and the turbidity measurements may be the same or different.

It is noted that when the temperature/conductivity/turbidity sensors and/or temperature/conductivity/turbidity measurements are defined as being positioned/performed "within" a milk meter, this is meant to cover temperature/conductivity/turbidity sensors, as well as temperature/conductivity measurements performed by said temperature/conductivity/turbidity sensors, positioned/performed in any part of the milk meter itself, as well as temperature/conductivity/turbidity sensors/measurements positioned/performed in the vicinity thereof, e.g., in tubes connecting to the milk meter, and the like. It is further noted that the above is defined for any other possible sensor utilized within the system.

According to some embodiments, the method for monitoring a CIP wash procedure in a milk farm further comprises:

comparing the obtained temperature measurements to at least one predefined temperature value stored in the computer system;

comparing the obtained conductivity measurements to at least one predefined conductivity value stored in the computer system;

comparing the obtained turbidity measurements to at least one predefined turbidity value stored in the computer system;

generating a temperature alert when a deviation between the obtained temperature measurements and the predefined temperature values is above about a pre-defined temperature threshold;

generating a conductivity alert when a deviation between the obtained conductivity measurements and the predefined conductivity values is above about a predefined conductivity threshold;

generating a turbidity alert when a deviation between the obtained turbidity measurements and the predefined turbidity values is above about a pre-defined turbidity threshold; or any combination thereof.

Figure 3:
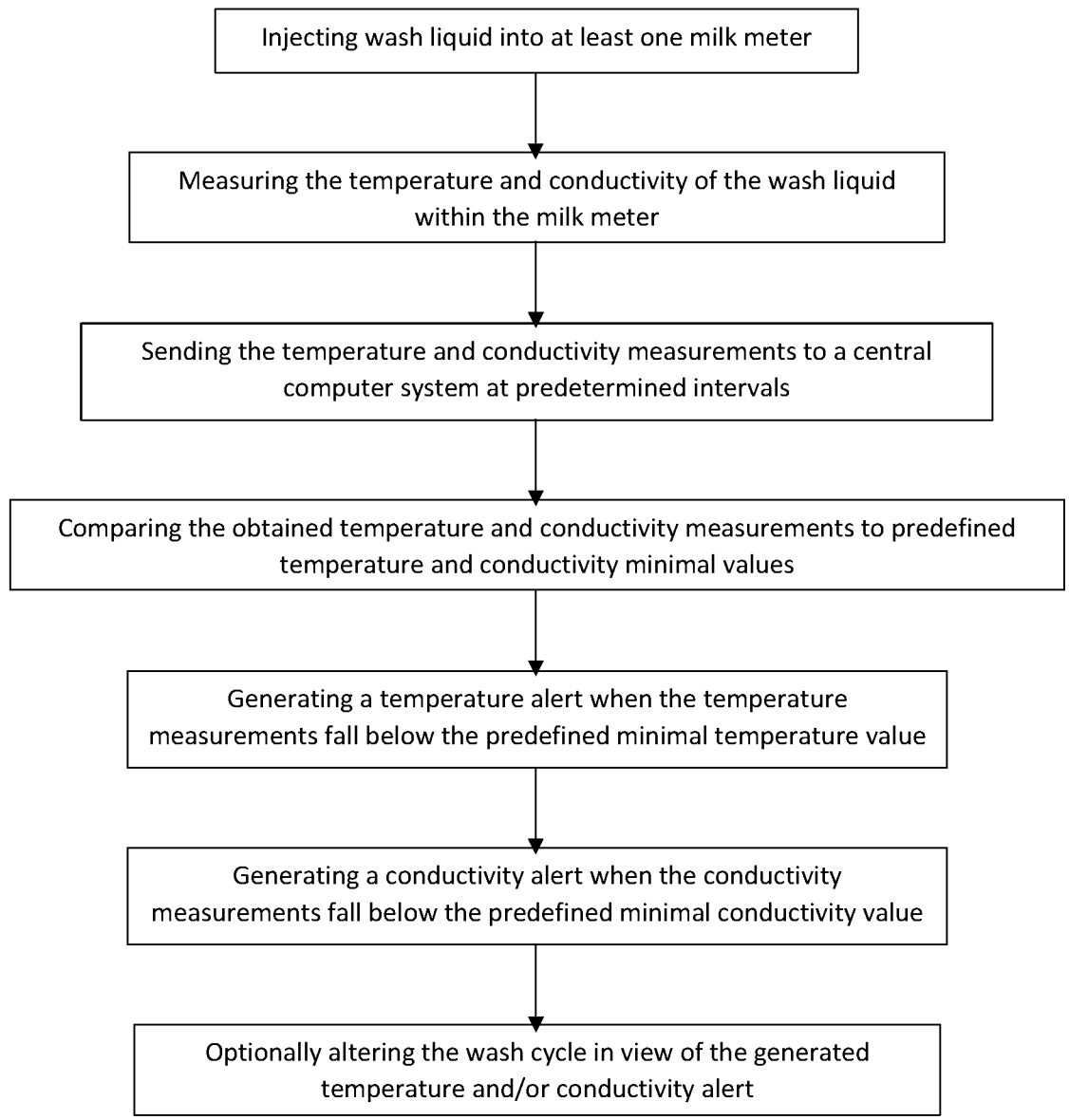
FIG. 3 presents a flow chart illustrating an embodiment of the method of the invention utilizing both temperature and conductivity sensors.
Figure 4:
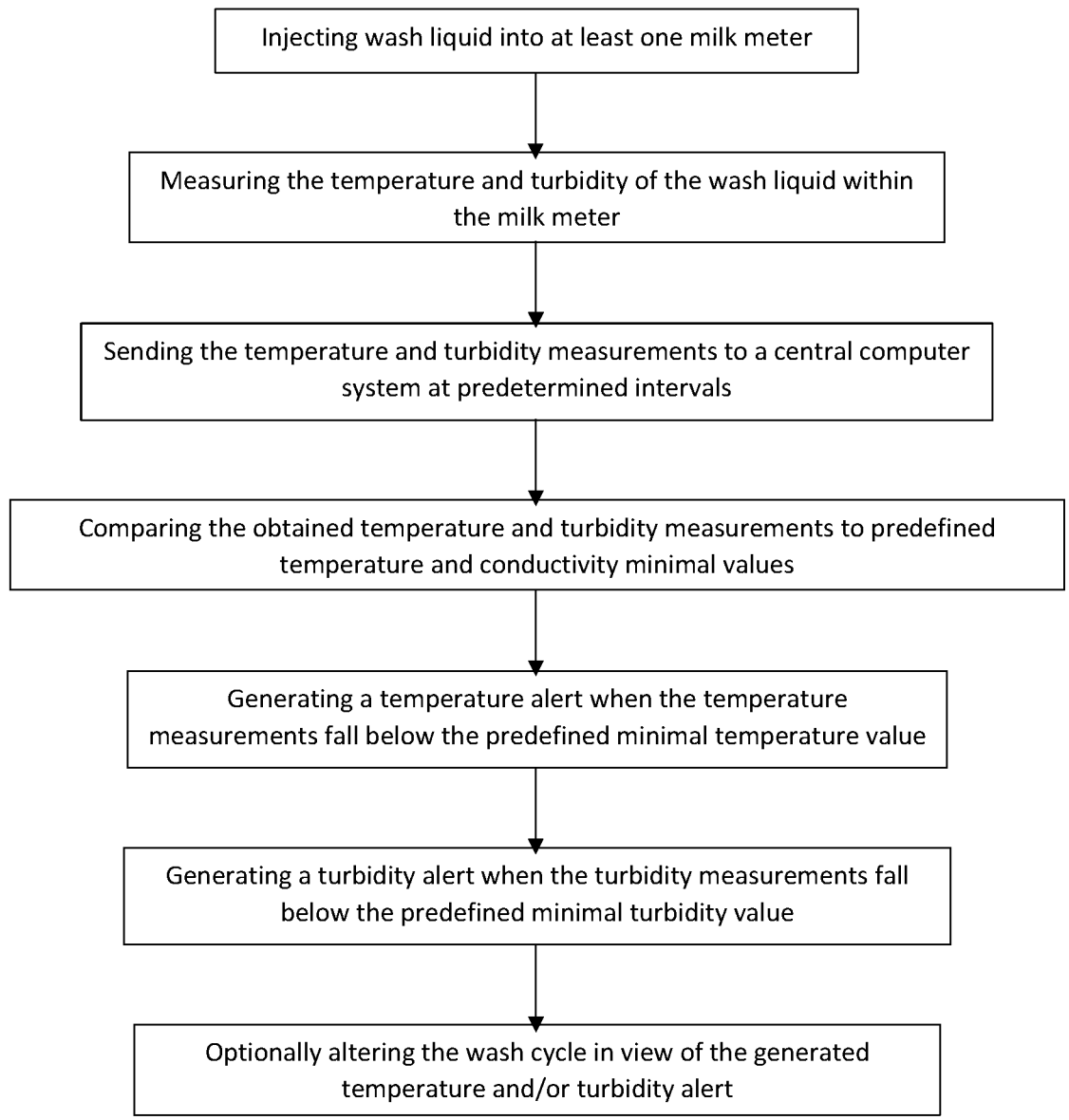
FIG. 4 presents a flow chart illustrating an embodiment of the method of the invention utilizing both temperature and turbidity sensors.
Figure 5:
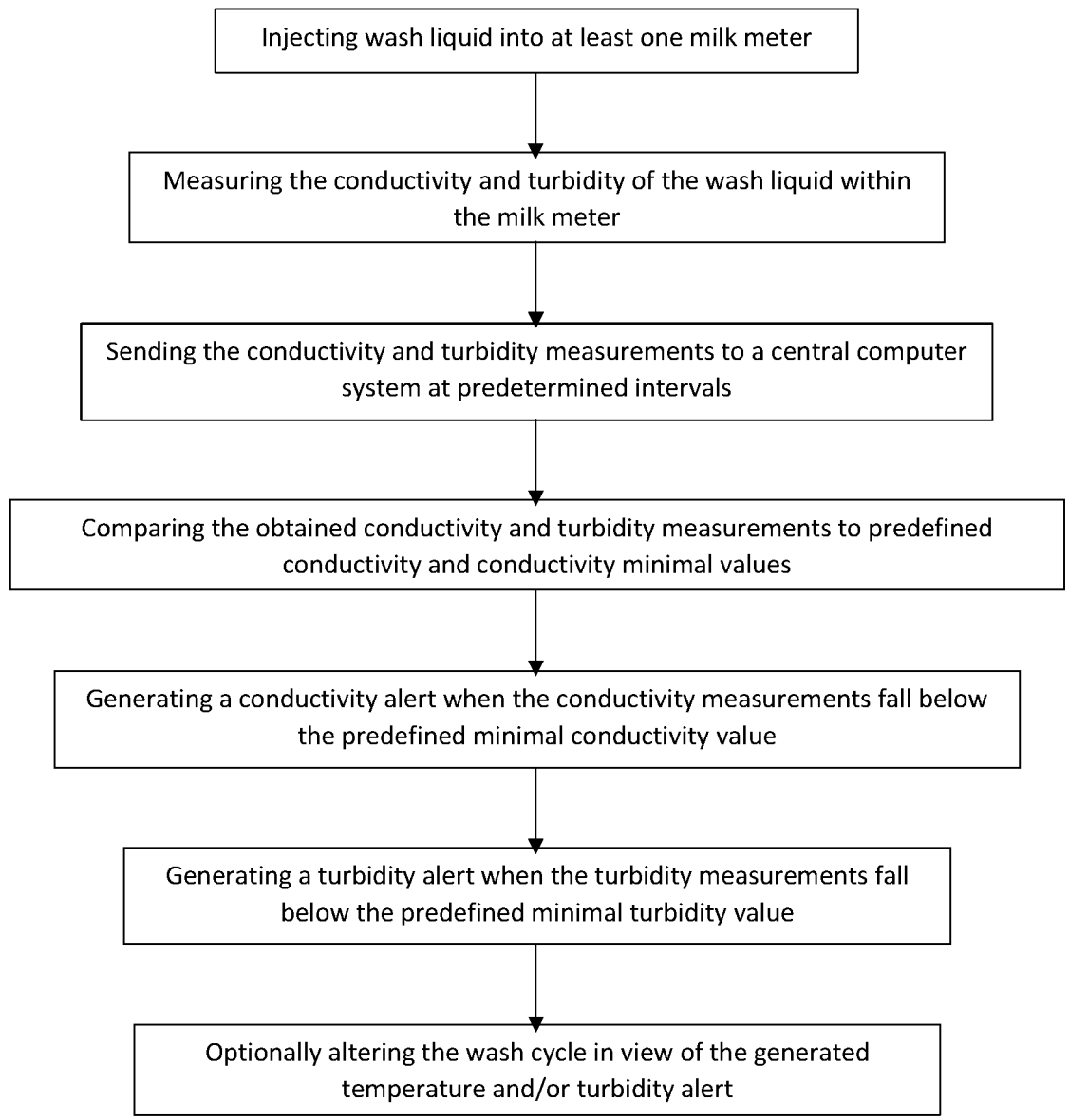
FIG. 5 presents a flow chart illustrating an embodiment of the method of the invention utilizing both conductivity and turbidity sensors.
Figure 6:
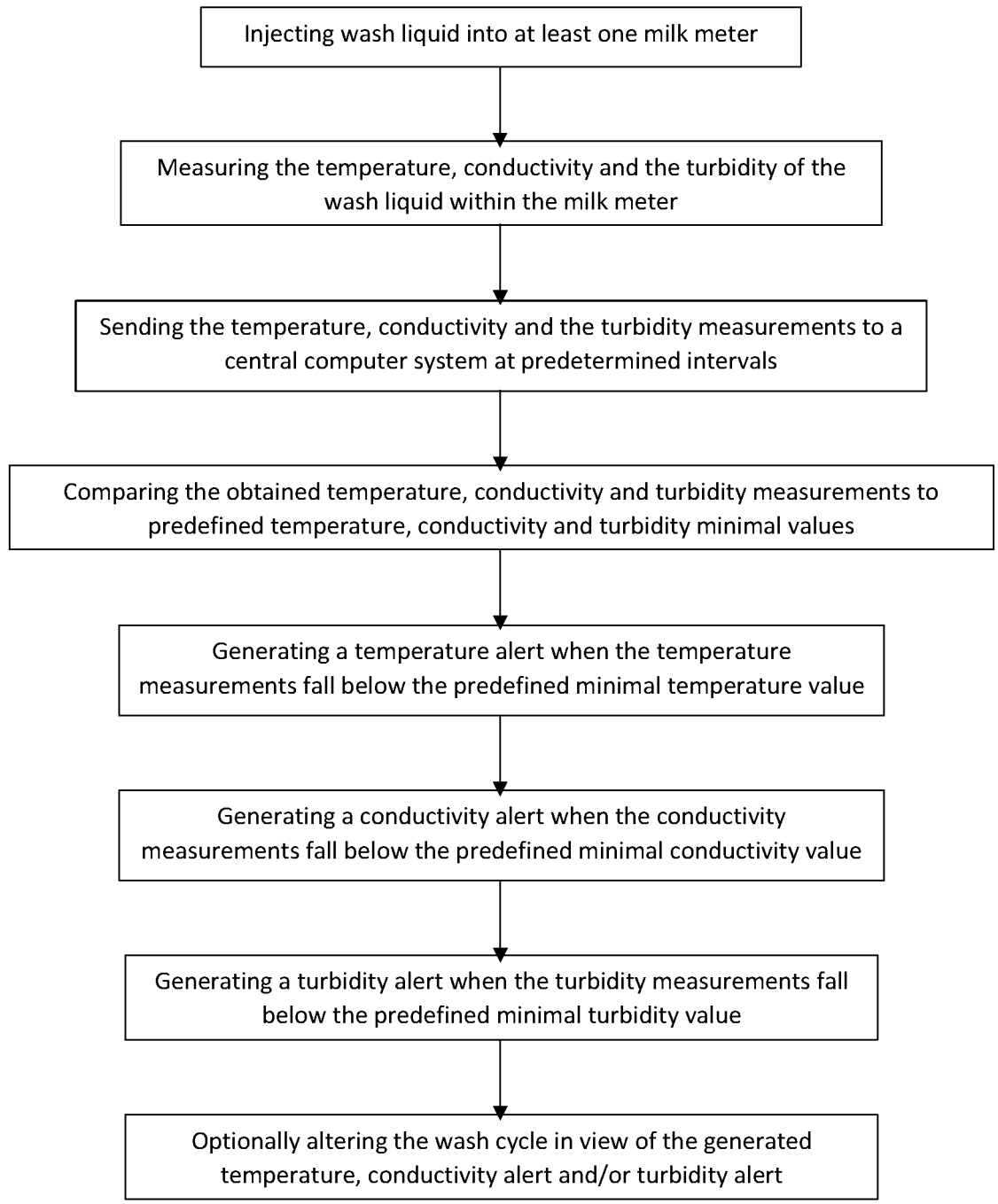
FIG. 6 presents a flow chart illustrating an embodiment of the method of the invention utilizing both temperature, conductivity and turbidity sensors.

FIGS. 3-6 present flowcharts in which the above embodiments of the method of the invention are illustrated, wherein FIG. 3 illustrates a method in which temperature and conductivity sensors are utilized, FIG. 4 illustrates a method in which temperature and turbidity sensors are utilized, FIG. 5 illustrates a method in which conductivity and turbidity sensors are utilized and FIG. 6 illustrates a method in which temperature, conductivity and turbidity sensors are utilized.

According to some embodiments, the method comprises calculating the pH of the wash fluid according to the conductivity measurements. It is noted that rather than comparing conductivity measurements to conductivity predefined values, pH values, calculated from conductivity measurements, may be compared to at least one predefined pH value. Further, alerts may be generated when a deviation between the calculated pH values and at least one predefined pH value is above about a predefined pH threshold.

Additional embodiments of the invention are directed to a method for monitoring a CIP wash procedure in a milk farm, wherein the method comprises:

measuring the temperature of the wash fluid by way of a temperature sensor positioned within each milk meter in a plurality of milk meters, thereby obtaining temperature measurements;

measuring the conductivity of the wash fluid by way of a conductivity sensor positioned within each milk meter in a plurality of milk meters, thereby obtaining conductivity measurements;

sending the temperature measurements and conductivity measurements from each temperature sensor and conductivity sensor to a central computer system at pre-defined time intervals, wherein the time intervals for sending the temperature measurements may be the same or different than the time intervals for sending the conductivity measurements;

calculating the length of time during which the temperature measurements are within about a predetermined temperature range, thereby obtaining a temperature time length measurement; and calculating the length of time during which the conductivity measurements are within about a predetermined conductivity range, thereby obtaining a conductivity time length measurement.

According to some embodiments, the method for monitoring a CIP wash procedure in a milk farm further comprises:

comparing the obtained temperature measurements to at least one predefined temperature value stored in the computer system;

comparing the obtained conductivity measurements to at least one predefined conductivity value stored in the computer system;

comparing the temperature time length measurement to at least one predefined temperature time length value stored in the computer system;

comparing the conductivity time length measurement to at least one predefined conductivity time length value stored in the computer system;

generating a temperature alert when a deviation between the temperature measurement and the pre-defined temperature value is above about a predefined temperature threshold;

generating a conductivity alert when a deviation between the conductivity measurement and the pre-defined conductivity value is above about a predefined conductivity threshold;

generating a temperature time alert when a deviation between the temperature time length measurement and the predefined temperature time length value is above about a pre-defined temperature time threshold;

generating a conductivity time alert when a deviation between the conductivity time length measurement and the predefined conductivity time length value is above about a pre-defined conductivity time threshold; or any combination thereof.

Figure 7:
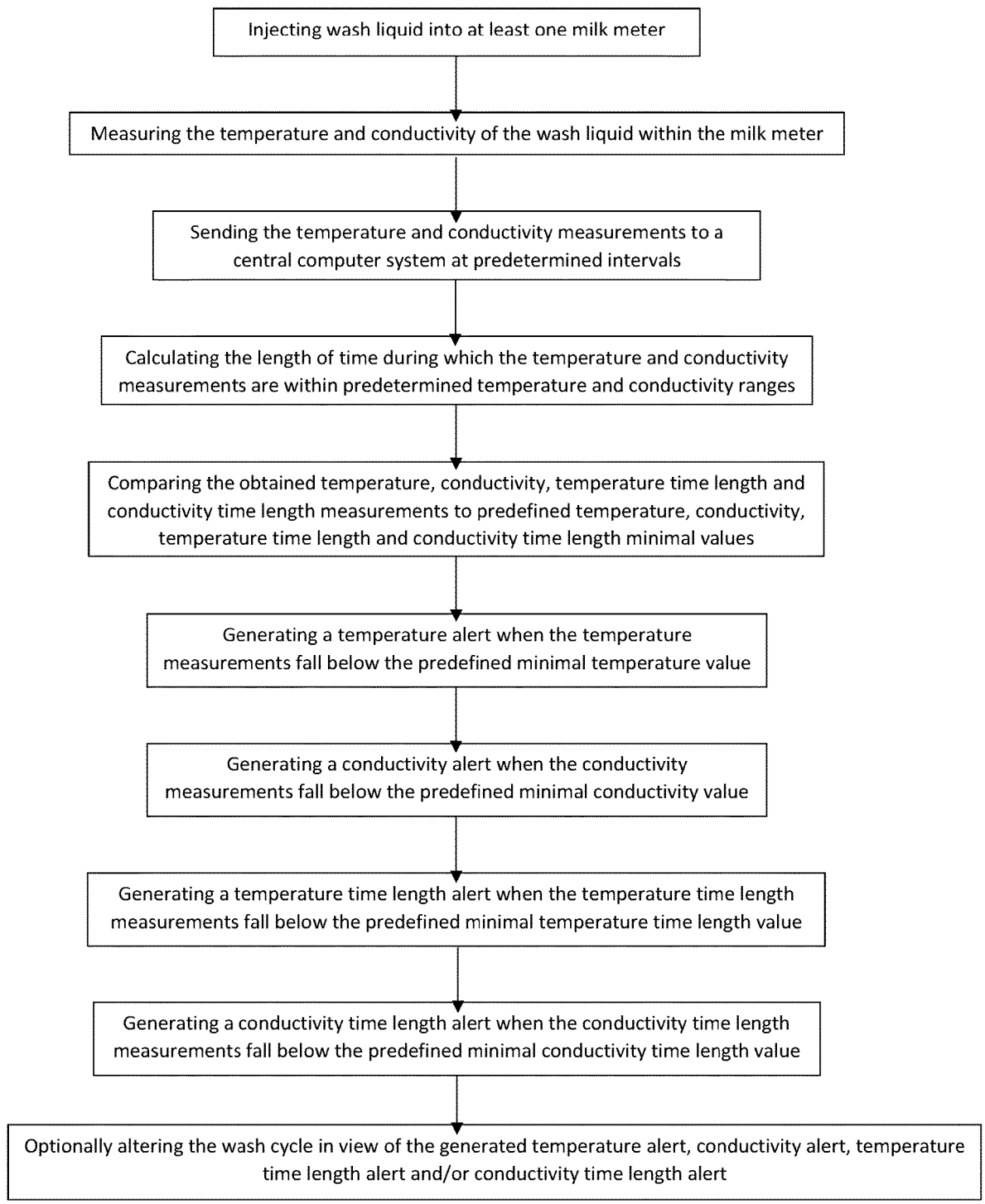
FIG. 7 presents a flow chart detailing an embodiment of the method of the invention, utilizing temperature and conductivity measurements and time calculations.

FIG. 7 presents a flowchart in which the above embodiment of the method of the invention is illustrated.

Additional embodiments of the invention are directed to a method for monitoring a CIP wash procedure in a milk farm, wherein the method comprises:

measuring the temperature of the wash fluid by way of a temperature sensor positioned within each milk meter in a plurality of milk meters, thereby obtaining temperature measurements;

measuring the turbidity of the wash fluid by way of a turbidity sensor positioned within each milk meter in a plurality of milk meters, thereby obtaining turbidity measurements;

sending the temperature measurements and turbidity measurements from each temperature sensor and turbidity sensor to a central computer system at pre-defined time intervals, wherein the time intervals for sending the temperature measurements may be the same or different than the time intervals for sending the turbidity measurements;

calculating the length of time during which the temperature measurements are within about a predetermined temperature range, thereby obtaining a temperature time length measurement; and calculating the length of time during which the turbidity measurements are within about a predetermined turbidity range, thereby obtaining a turbidity time length measurement.

According to some embodiments, the method for monitoring a CIP wash procedure in a milk farm further comprises:

comparing the obtained temperature measurements to at least one predefined temperature value stored in the computer system;

comparing the obtained turbidity measurements to at least one predefined turbidity value stored in the computer system;

comparing the temperature time length measurement to at least one predefined temperature time length value stored in the computer system;

comparing the turbidity time length measurement to at least one predefined turbidity time length value stored in the computer system;

generating a temperature alert when a deviation between the temperature measurement and the pre-defined temperature value is above about a predefined temperature threshold;

generating a turbidity alert when a deviation between the turbidity measurement and the pre-defined turbidity value is above about a predefined turbidity threshold;

generating a temperature time alert when a deviation between the temperature time length measurement and the predefined temperature time length value is above about a pre-defined temperature time threshold;

generating a turbidity time alert when a deviation between the turbidity time length measurement and the pre-defined turbidity time length value is above about a pre-defined turbidity time threshold; or any combination thereof.

Figure 8:
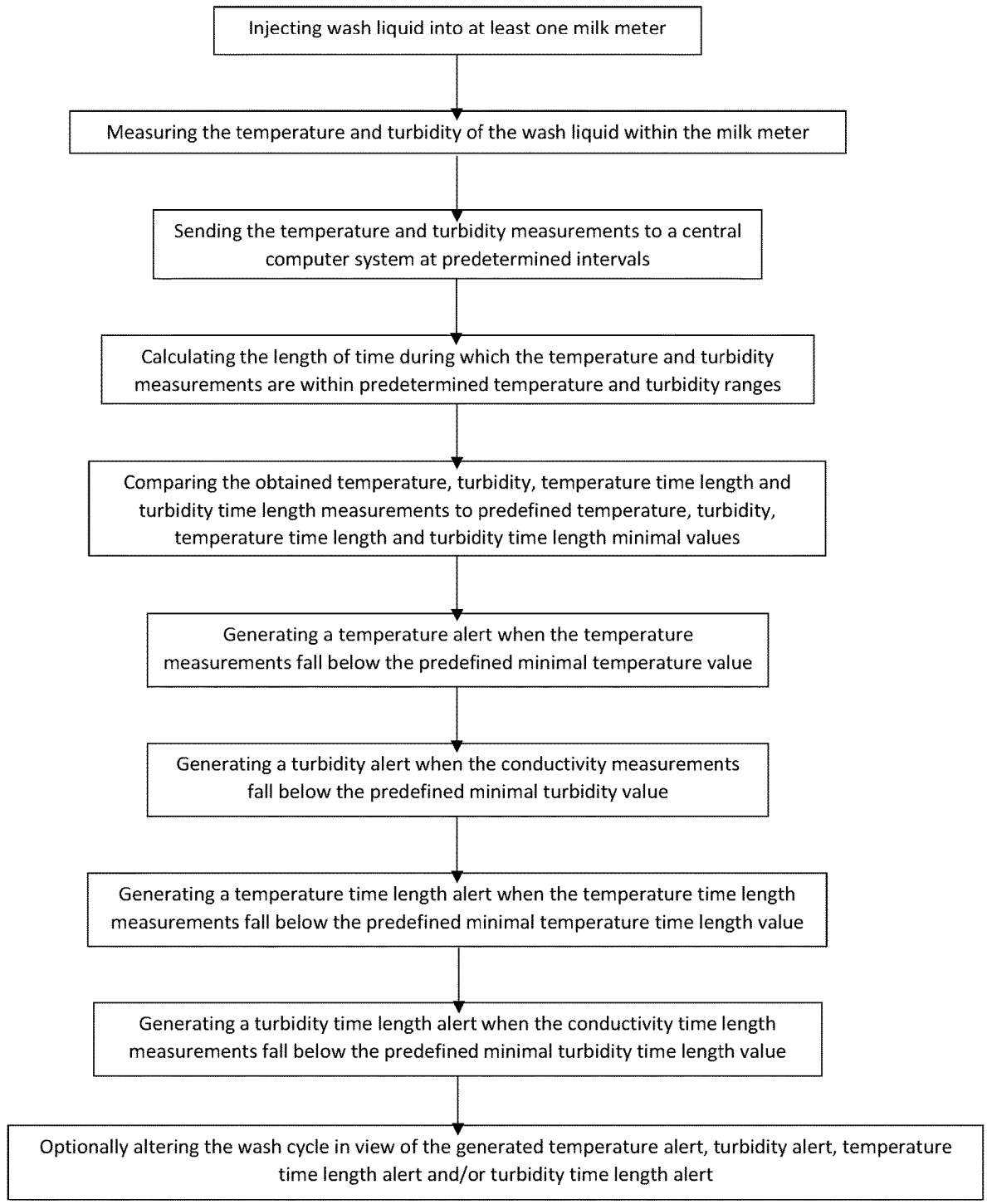
FIG. 8 presents a flow chart detailing an embodiment of the method of the invention, utilizing temperature and turbidity measurements and time calculations.

FIG. 8 presents a flowchart in which the above embodiment of the method of the invention is illustrated.

Additional embodiments of the invention are directed to a method for monitoring a CIP wash procedure in a milk farm, wherein the method comprises:

measuring the turbidity of the wash fluid by way of a turbidity sensor positioned within each milk meter in a plurality of milk meters, thereby obtaining turbidity measurements;

measuring the conductivity of the wash fluid by way of a conductivity sensor positioned within each milk meter in a plurality of milk meters, thereby obtaining conductivity measurements;

sending the turbidity measurements and conductivity measurements from each turbidity sensor and conductivity sensor to a central computer system at pre-defined time intervals, wherein the time intervals for sending the turbidity measurements may be the same or different than the time intervals for sending the conductivity measurements;

calculating the length of time during which the turbidity measurements are within about a predetermined turbidity range, thereby obtaining a turbidity time length measurement; and calculating the length of time during which the conductivity measurements are within about a predetermined conductivity range, thereby obtaining a conductivity time length measurement.

According to some embodiments, the method for monitoring a CIP wash procedure in a milk farm further comprises:

comparing the obtained turbidity measurements to at least one predefined turbidity value stored in the computer system;

comparing the obtained conductivity measurements to at least one predefined conductivity value stored in the computer system;

comparing the turbidity time length measurement to at least one predefined turbidity time length value stored in the computer system;

comparing the conductivity time length measurement to at least one predefined conductivity time length value stored in the computer system;

generating a turbidity alert when a deviation between the turbidity measurement and the pre-defined turbidity value is above about a predefined turbidity threshold;

generating a conductivity alert when a deviation between the conductivity measurement and the pre-defined conductivity value is above about a predefined conductivity threshold;

generating a turbidity time alert when a deviation between the turbidity time length measurement and the pre-defined turbidity time length value is above about a pre-defined turbidity time threshold;

generating a conductivity time alert when a deviation between the conductivity time length measurement and the predefined conductivity time length value is above about a pre-defined conductivity time threshold; or any combination thereof.

Figure 9:
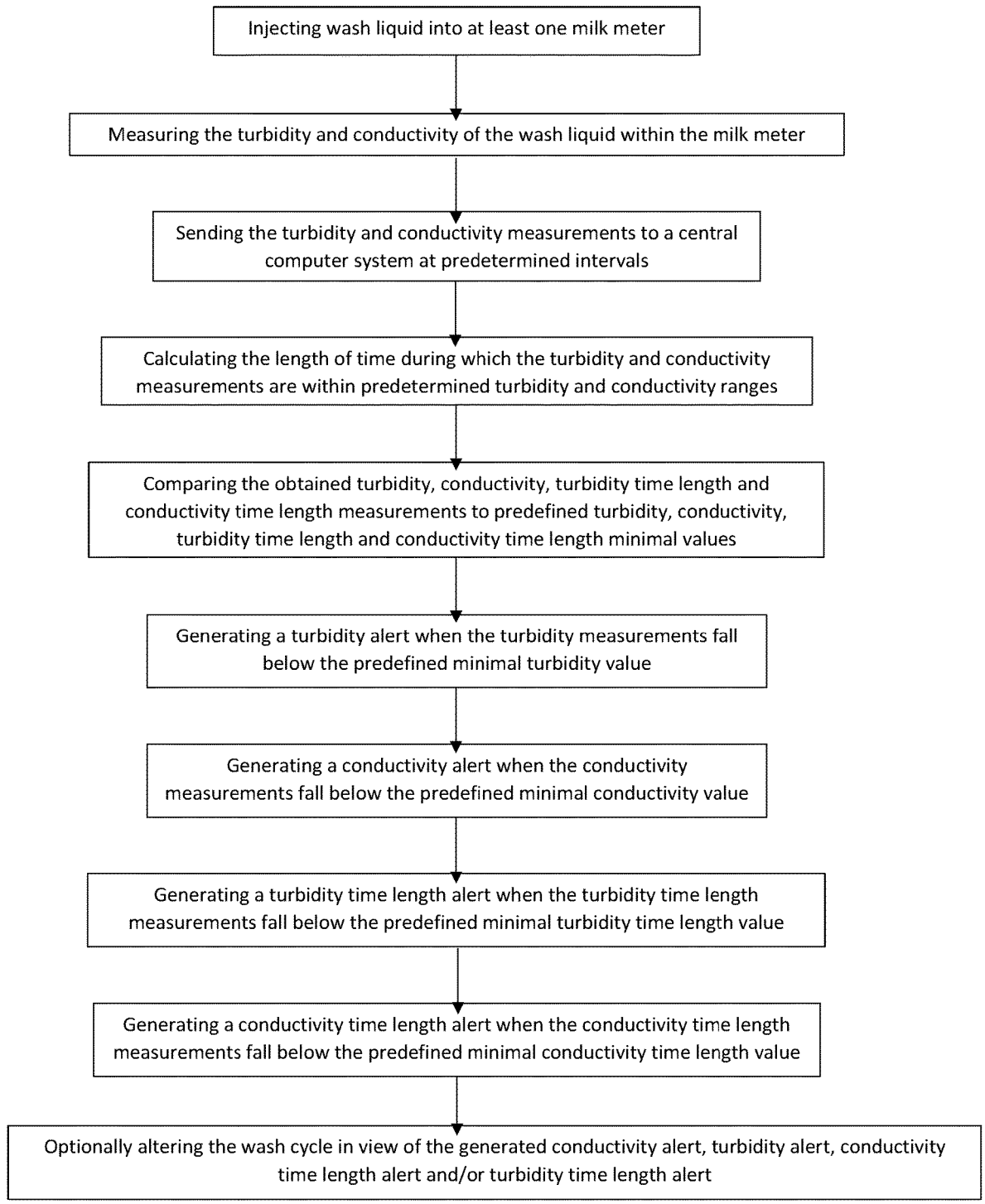
FIG. 9 presents a flow chart detailing an embodiment of the method of the invention, utilizing conductivity and turbidity measurements and time calculations.

FIG. 9 presents a flowchart in which the above embodiment of the method of the invention is illustrated.

Additional embodiments of the invention are directed to a method for monitoring a CIP wash procedure in a milk farm, wherein the method comprises:

measuring the temperature of the wash fluid by way of a temperature sensor positioned within each milk meter in a plurality of milk meters, thereby obtaining temperature measurements;

measuring the conductivity of the wash fluid by way of a conductivity sensor positioned within each milk meter in a plurality of milk meters, thereby obtaining conductivity measurements;

measuring the turbidity of the wash fluid by way of a turbidity sensor positioned within each milk meter in a plurality of milk meters, thereby obtaining turbidity measurements;

sending the temperature measurements, conductivity measurements and turbidity measurements from each temperature sensor, conductivity sensor and turbidity sensor to a central computer system at pre-defined time intervals, wherein the time intervals for sending the temperature measurements, conductivity measurements and turbidity measurements may be the same or different;

calculating the length of time during which the temperature measurements are within about a predetermined temperature range, thereby obtaining a temperature time length measurement;

calculating the length of time during which the conductivity measurements are within about a predetermined conductivity range, thereby obtaining a conductivity time length measurement; and calculating the length of time during which the turbidity measurements are within about a predetermined turbidity range, thereby obtaining a turbidity time length measurement.

According to some embodiments, the method for monitoring a CIP wash procedure in a milk farm further comprises:

comparing the obtained temperature measurements to at least one predefined temperature value stored in the computer system;

comparing the obtained conductivity measurements to at least one predefined conductivity value stored in the computer system;

comparing the obtained turbidity measurements to at least one predefined turbidity value stored in the computer system;

comparing the temperature time length measurement to at least one predefined temperature time length value stored in the computer system;

comparing the conductivity time length measurement to at least one predefined conductivity time length value stored in the computer system;

comparing the turbidity time length measurement to at least one predefined turbidity time length value stored in the computer system;

generating a temperature alert when a deviation between the temperature measurement and the pre-defined temperature value is above about a predefined temperature threshold;

generating a conductivity alert when a deviation between the conductivity measurement and the pre-defined conductivity value is above about a predefined conductivity threshold;

generating a turbidity alert when a deviation between the turbidity measurement and the pre-defined turbidity value is above about a predefined turbidity threshold;

generating a temperature time alert when a deviation between the temperature time length measurement and the predefined temperature time length value is above about a pre-defined temperature time threshold;

generating a conductivity time alert when a deviation between the conductivity time length measurement and the predefined conductivity time length value is above about a pre-defined conductivity time threshold;

generating a turbidity time alert when a deviation between the turbidity time length measurement and the predefined turbidity time length value is above about a pre-defined turbidity time threshold; or any combination thereof.

Figure 10:
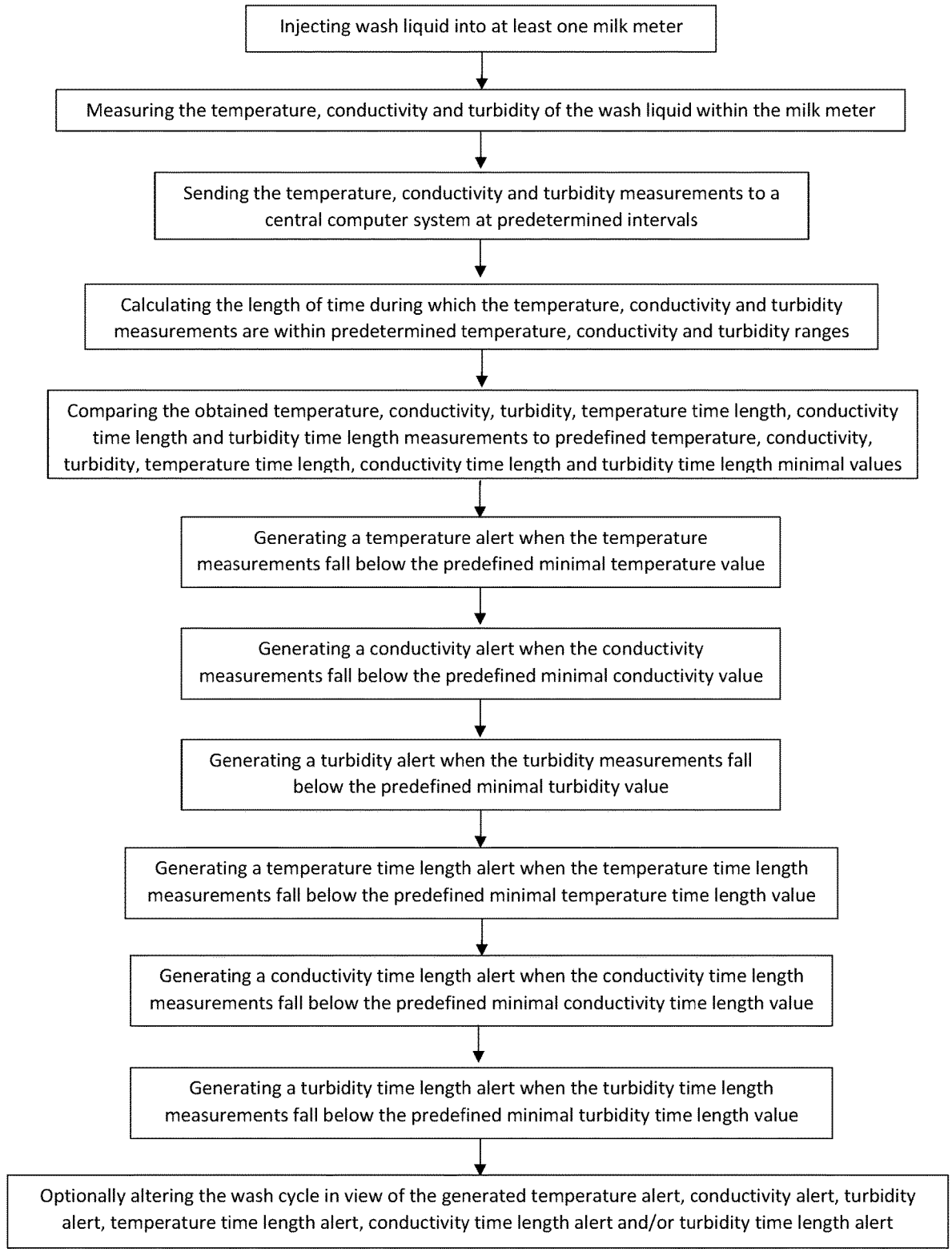
FIG. 10 presents a flow chart detailing an embodiment of the method of the invention, utilizing temperature, conductivity and turbidity measurements and time calculations.

FIG. 10 presents a flowchart in which the above embodiment of the method of the invention is illustrated.

According to some embodiments, any of the temperature, conductivity, turbidity and/or temperature/conductivity/turbidity time length thresholds defined herein, may be minimal values, wherein if the temperature measurements/conductivity measurements/turbidity measurements/temperature time length measurements/conductivity time length measurements/turbidity time length measurements fall below about a pre-defined minimal value, the system will generate an alert. It is noted that the above is defined for any type of time length measurements and thresholds calculated according to data received from any type of sensor utilized in the system.

According to some embodiments, the method of the invention includes a feedback system, which includes an "on-line wash procedure", such that during the CIP wash procedure, any of the set parameters of the CIP wash procedure may be changed according to measurements obtained during the wash from the temperature and/or conductivity and/or turbidity sensor(s) within the milk meter. For instance, if the temperature measurements and/or temperature time length measurements show that the hot liquid did not remain in the system, or in the entirety thereof, for at least a predetermined minimal length of time, e.g., due to cold external conditions, the wash cycle may be at least partially repeated and/or lengthened. Further, if the measurements show that the temperature of the hot washes in at least one milk meter is below about a certain predetermined temperature, the initial temperature of the wash fluid may be raised. Likewise, if the conductivity measurements show that the pH of the wash liquid is not within about an appropriate predetermined range or is below about a minimal value, the composition of the wash liquid may be adjusted, and/or the wash cycle may be at least partially repeated and/or lengthened. Similarly, if the turbidity measurements indicate that the wash fluid is contaminated, the wash cycle may be at least partially repeated with a fresh wash fluid.

The temperature measurements and/or the conductivity measurements and/or the turbidity measurements provided from the temperature/conductivity/turbidity sensors in the milk meter may aid in the quick detection of malfunctions in the system, e.g., within in a particular milk meter or the vicinity thereof. Accordingly, the method of the invention further includes detecting system malfunctions by analyzing the temperature measurements and/or the conductivity measurements and/or the turbidity measurements, thereby enabling those malfunctions to be quickly detected and attended to.

Unless explicitly stated, the method embodiments described herein are not constrained to a particular order or sequence. Additionally, some of the described method embodiments or elements thereof can occur or be performed simultaneously, at the same point in time, or concurrently.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

What is claimed is:

1. A system comprising:

a first plurality of milk meters, wherein each milk meter in the first plurality of milk meters comprises a temperature sensor; and a central computer system connected to the plurality of milk meters;

wherein the central computer system is connected physical or virtually to the milk meters and wherein the central computer system is configured to:

store at least one predefined temperature value, at least one predefined temperature time length value, at least one predefined temperature range, at least one predefined temperature threshold and at least one predefined temperature time length threshold;

receive and store temperature measurements from the temperature sensors;

compare the temperature measurements to the predefined temperature value;

calculate temperature time length measurements according to a time during which the temperature measurements are within about the predetermined temperature range;

generate a temperature alert when a deviation between the temperature measurements and the predefined temperature value is above about the predefined temperature threshold;

generate a temperature time alert when a deviation between the temperature time length measurements and the predefined temperature time length value is above about the predefined temperature time length threshold, and wherein said system comprises a second plurality of milk meters, wherein each milk meter in the second plurality of milk meters comprises a conductivity sensor; and wherein the central computer system is further configured to:

store at least one predefined conductivity value, at least one predefined conductivity time length value, at least one predefined conductivity range, at least one predefined conductivity threshold and at least one predefined conductivity time length threshold;

receive and store conductivity measurements from the conductivity sensors;

compare the conductivity measurements to the predefined conductivity value;

calculate conductivity time length measurements according to a time during which the conductivity measurements are within about the predetermined conductivity range;

generate conductivity alerts when a deviation between the conductivity measurements and the predefined conductivity value is above about the predefined conductivity threshold;

generate conductivity time alerts when a deviation between the conductivity time length measurements and the predefined conductivity time length values is above about the predefined conductivity time length threshold.

2. The system according to claim 1, wherein the first plurality of milk meters and the second plurality of milk meters are the same, such that each milk meter includes both a temperature sensor and a conductivity sensor.

3. A system comprising:
a first plurality of milk meters, wherein each milk meter in the first plurality of milk meters comprises a temperature sensor; and
a central computer system connected to the plurality of milk meters;
wherein the central computer system is connected physical or virtually to the milk meters and wherein the central computer system is configured to:
store at least one predefined temperature value, at least one predefined temperature time length value, at least one predefined temperature range, at least one predefined temperature threshold and at least one predefined temperature time length threshold;
receive and store temperature measurements from the temperature sensors;
compare the temperature measurements to the predefined temperature value;
calculate temperature time length measurements according to a time during which the temperature measurements are within about the predetermined temperature range;
generate a temperature alert when a deviation between the temperature measurements and the predefined temperature value is above about the predefined temperature threshold;
generate a temperature time alert when a deviation between the temperature time length measurements and the predefined temperature time length value is above about the predefined temperature time length threshold, and
wherein said system further comprises a third plurality of milk meters, wherein
each milk meter in the third plurality of milk meters comprises a turbidity sensor; and
wherein the central computer system is further configured to:
store at least one predefined turbidity value, at least one predefined turbidity time length value, at least one predefined turbidity range, at least one predefined turbidity threshold and at least one predefined turbidity time length threshold;
receive and store turbidity measurements from the conductivity sensors;
compare the turbidity measurements to the predefined conductivity value;
calculate turbidity time length measurements according to a time during which the turbidity measurements are within about the predetermined turbidity range;
generate turbidity alerts when a deviation between the turbidity measurements and the predefined turbidity value is above about the predefined turbidity threshold;
generate turbidity time alerts when a deviation between the turbidity time length measurements and the predefined turbidity time length values is above about the predefined turbidity time length threshold.

4. The system according to claim 3, wherein the first plurality of milk meters, the second plurality of milk meters and the third plurality of milk meters are the same, such that each milk meter includes a temperature sensor, a conductivity sensor and a turbidity sensor.

5. A method for monitoring a clean in place (CIP) wash procedure in a milk farm, wherein the method comprises:
measuring the temperature of a wash fluid by way of a temperature sensor positioned within each milk meter in a first plurality of milk meters, thereby obtaining temperature measurements;
measuring the conductivity of the wash fluid by way of a conductivity sensor positioned within each milk meter in a second plurality of milk meters, thereby obtaining conductivity measurements;
sending the temperature measurements and conductivity measurements from each temperature sensor and each conductivity sensor to a central computer system at pre-defined time intervals, wherein the time intervals for sending the temperature measurements may be the same or different than the time intervals for sending the conductivity measurements;
calculating the length of time during which the temperature measurements are within about a predetermined temperature range, thereby obtaining a temperature time length measurement; and
calculating the length of time during which the conductivity measurements are within about a predetermined conductivity range, thereby obtaining a conductivity time length measurement,
wherein the first plurality of milk meters and the second plurality of milk meters may be the same or different,
wherein said method further comprises:
generating a temperature alert when a deviation between the temperature measurement and the pre-defined temperature value is above about a predefined temperature threshold;
generating a conductivity alert when a deviation between the conductivity measurement and the pre-defined conductivity value is above about a predefined conductivity threshold;
generating a temperature time alert when a deviation between the temperature time length measurement and the predefined temperature time length values is above about a pre-defined temperature time threshold;
generating a conductivity time alert when a deviation between the conductivity time length measurement and the predefined conductivity time length values is above about a pre-defined conductivity time threshold; or
any combination thereof.

6. The method according to claim 5, wherein said method further comprises altering the CIP wash procedure according to the temperature alerts, the temperature time alerts, the conductivity alerts, the conductivity time alerts, or any combination thereof.

7. A method for monitoring a clean in place (CIP) wash procedure in a milk farm, wherein the method comprises:
measuring the temperature of a wash fluid by way of a temperature sensor positioned within each milk meter in a first plurality of milk meters, thereby obtaining temperature measurements;
measuring the conductivity of the wash fluid by way of a conductivity sensor positioned within each milk meter in a second plurality of milk meters, thereby obtaining conductivity measurements;
sending the temperature measurements and conductivity measurements from each temperature sensor and each conductivity sensor to a central computer system at pre-defined time intervals, wherein the time intervals for sending the temperature measurements may be the same or different than the time intervals for sending the conductivity measurements;

calculating the length of time during which the temperature measurements are within about a predetermined temperature range, thereby obtaining a temperature time length measurement; and calculating the length of time during which the conductivity measurements are within about a predetermined conductivity range, thereby obtaining a conductivity time length measurement, wherein the first plurality of milk meters and the second plurality of milk meters may be the same or different;

wherein said method further comprises:

measuring the turbidity of the wash fluid by way of a turbidity sensor positioned within each milk meter in a third plurality of milk meters, thereby obtaining turbidity measurements;

sending the turbidity measurements from each turbidity sensor to a central computer system at pre-defined time intervals, wherein the time intervals for sending the temperature measurements, conductivity measurements and turbidity measurements may be the same or different; and calculating the length of time during which the turbidity measurements are within about a predetermined turbidity range, thereby obtaining a turbidity time length measurement, wherein the first plurality of milk meters, the second plurality of milk meters and the third plurality of milk meters may be the same or different.

8. The method according to claim 7, wherein said method further comprises:

generating a turbidity alert when a deviation between the turbidity measurement and the pre-defined turbidity value is above about a predefined turbidity threshold;

generating a turbidity time alert when a deviation between the turbidity time length measurement and the pre-defined turbidity time length values is above about a pre-defined turbidity time threshold; or any combination thereof.

* * * * *